US006916659B2

(12) United States Patent
Gropp

(10) Patent No.: US 6,916,659 B2
(45) Date of Patent: Jul. 12, 2005

(54) METHOD FOR TREATING OBJECTS

(75) Inventor: Robert Gropp, Schifferstadt (DE)

(73) Assignee: Leica Microsystems Nussloch GmbH, Nussloch (DE)

(*) Notice: Subject to any disclaimer, the term of this patent is extended or adjusted under 35 U.S.C. 154(b) by 497 days.

(21) Appl. No.: 10/004,092

(22) Filed: Oct. 23, 2001

(65) Prior Publication Data
US 2002/0111743 A1 Aug. 15, 2002

(30) Foreign Application Priority Data
Oct. 24, 2000 (DE) .......................................... 100 52 832

(51) Int. Cl.[7] .......................... B01L 3/02; G05B 19/04
(52) U.S. Cl. ............................ 436/50; 422/99; 422/100
(58) Field of Search ............................ 422/99, 100, 67; 436/50, 55, 43, 47, 48; 702/19

(56) References Cited
U.S. PATENT DOCUMENTS 5,153,839 A * 10/1992 Cross .......................... 700/112
5,737,499 A * 4/1998 Bernstein et al. ........... 700/247
5,895,628 A    4/1999 Heid et al. ..................... 422/65

* cited by examiner

Primary Examiner—Jill Warden
Assistant Examiner—Jyoti Nagpaul
(74) Attorney, Agent, or Firm—Hodgson Russ LLP

(57) ABSTRACT

A method for treating objects, in particular cytological or histological specimens, for example in an automatic stainer, the objects being delivered, preferably on object carriers and in object carrier magazines, by means of a transport device to various processing stations, inserted therein, and treated in accordance with a definable treatment program, and the transport device being capable, during the treatment, of moving further objects or object carriers to other processing stations so that a parallel processing or treatment is possible in various processing stations, is characterized by an optimized automatic program sequence according to which identically operating processing stations are defined as backup stations and are correspondingly occupied if a concretely required processing station is occupied.

4 Claims, 1 Drawing Sheet

METHOD FOR TREATING OBJECTS

CROSS REFERENCE TO RELATED APPLICATIONS

This invention claims priority of the German patent application 100 52 832.5 filed Oct. 24, 2000 which is incorporated by reference herein.

FIELD OF THE INVENTION

The present invention concerns a method for treating objects, in particular cytological or histological specimens, for example in an automatic stainer, the objects being delivered, preferably on object carriers and in object carrier magazines, by means of a transport device to various processing stations, inserted therein, and treated in accordance with a definable treatment program, and the transport device being capable, during the treatment, of moving further objects or object carriers to other processing stations so that a parallel processing or treatment is possible in various processing stations.

BACKGROUND OF THE INVENTION

The reader is referred, merely by way of example, to EP 0 849 582 A1. This document discloses a generic method for treating objects, in particular cytological or histological specimens. In it, cytological or histological specimens are conveyed, by means of an object carrier or basket and optionally in magazines, to the differently operating treatment stations of an automatic stainer, the stainer comprising multiple processing stations having different reagents.

The generic method known from EP 0 849 582 A1 refers to an automatic stainer (multistainer), this being concretely an apparatus for staining histological specimens. These specimens are made available on an object carrier, and multiple object carriers can be arranged in magazines. The different treatment or processing stations are reached via a transport apparatus that can comprise a robot arm. The transport apparatus transports the object carriers or object carrier magazines to the respective treatment stations, at or in which treatment actions take place in accordance with a selectable staining method. The object carriers or object carrier magazines are inserted into the reagent-containing containers of the treatment stations so that the transport apparatus, after releasing the respective object carrier or object carrier magazine, can continue transporting irrespective of the treatment that is taking place. During the processing time in a treatment station, further object carriers are grasped and can be delivered into an available treatment station, so that multiple staining programs can be executed in parallel.

With the known automatic stainers, the desired staining programs can be programmed by the user, multiple program steps being provided. Each individual program step contains numerous parameters, for example including information about the treatment station and how it is loaded with reagents, and the treatment time.

In automatic stainers known heretofore, only one treatment station can be specified per program step, double occupancy of the treatment station being precluded. In the context of a (desirable) parallel processing of multiple object carrier magazines (racks) that are to be stained, this results in bottlenecks because of the treatment stations that are critical in this context, thereby very considerably limiting throughput.

This can easily be demonstrated with reference to the single FIGURE, specifically if, in a program illustrated schematically therein, a treatment station is indicated in the first program step with a processing time of, for example, ten minutes, and multiple object carrier magazines are to be treated simultaneously with the staining program of this treatment station. Until now only serial processing, for example on a ten minute cycle, was possible in this context, and throughput was thereby very considerably limited.

SUMMARY OF THE INVENTION

It is thus the object of the present invention to configure and further develop a generic method for treating objects, in particular cytological or histological specimens, in such a way that even in the context of long treatment times in individual processing or treatment stations, efficient processing with an optimized program sequence is possible.

DETAILED DESCRIPTION OF THE INVENTION

Figure 1:
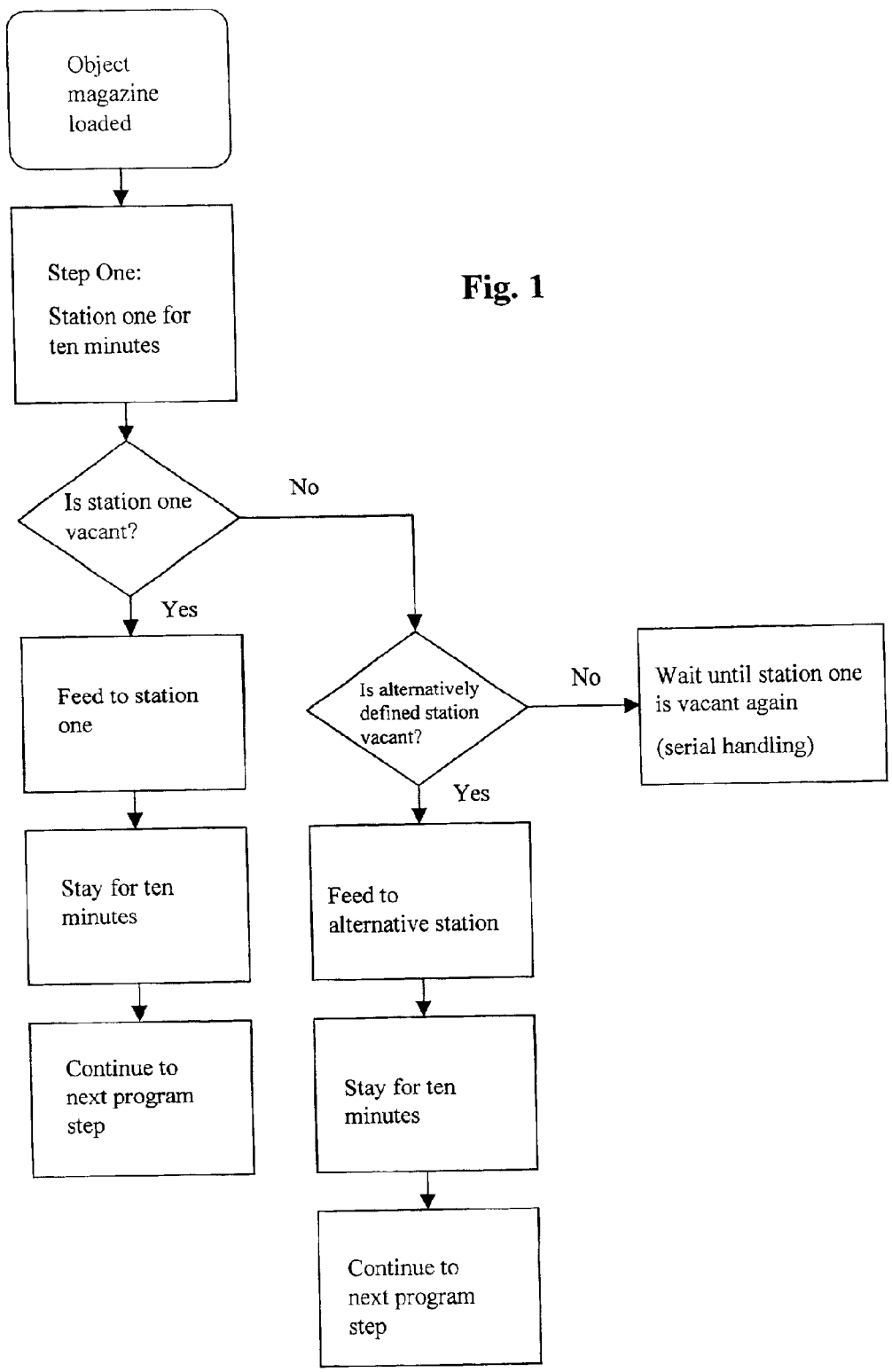
FIG. 1 is a schematic flow diagram of an automatic program sequence in accordance with the present invention.

According to the present invention, a generic method for treating objects, in particular cytological and histological specimens, is characterized by an optimized automatic program sequence according to which identically operating processing stations are defined as backup stations and are correspondingly utilized or occupied if a concretely required processing station is already occupied.

What has been recognized according to the present invention is firstly that an optimization of the automatic program sequence is possible if—especially in the context of critical processing stations, i.e. processing stations with a long treatment duration that are frequently needed—backup stations are made available, a backup station being defined as an identically operating processing/treatment station. This is made possible by generating a corresponding program sequence, especially since in a conventional automatic stainer multiple identically operating treatment stations are in any case provided. A backup station can correspondingly be occupied when a concretely required processing station is currently occupied, i.e. when processing or treatment is taking place.

The backup station is ultimately an alternative treatment station with an identical function, the feature claimed here making possible uniform utilization of the individual treatment stations.

Concretely, the processing program could take into account a priority list of identically operating processing stations as backup stations. This priority list for backup stations could be definable in any desired way by the user, an incorporation into the automatic program sequence or into the program responsible therefor taking place after definition of this priority list.

The priority list for backup stations could likewise be selectable as a defined program sequence from a file that is made available. In very particularly advantageous fashion, the priority list can be calculated in consideration of defined or definable parameters.

Concretely, the calculation of the priority list could be accomplished in consideration of shortest paths or in consideration of shortest transport times. It is very particularly advantageous if the calculation of the priority list is accomplished in consideration of current consumption data, expiration data, fill levels, or the like in the processing stations. The priority list could in particular be calculated, in consideration of the fill levels and consumption data in the processing stations, in such a way that in all identically operating processing stations, i.e. in the backup stations, an approximately identical consumption and thus also approximately identical fill level can be achieved on the basis of uniform utilization of the respective processing stations.

It has already been indicated several times previously that the processing stations can be reagent-equipped processing stations, water stations, heating stations or ovens, or the like, of an automatic stainer.

Let it be noted at this juncture that "stations" are understood very generally as the unloading station, loading station, and processing station of an automatic stainer. The processing stations can in turn be reagent stations, oven/heating stations, or water stations.

In the context of an embodiment according to the present invention it is possible, in the execution of the staining programs, to divert to alternative processing stations or backup stations that are loaded with the same reagents and thus have the same function. The backup stations can be selected, in this context, explicitly by the user upon programming of the staining program, or independently or automatically by the unit on the basis of a known and/or definable reagent filling. This is advantageous in particular for treatment stations with very long processing times.

As already mentioned previously, when the alternative station designated as a backup station is selected, it is possible to perform a priority control according to which the sequence in which the possible backup stations are used is stipulated. The definition of the priorities is determined either explicitly by the user of the automatic stainer or (automatically) by the unit. The sequence or ranking order of the treatment stations to be used alternatively is selected or defined on the basis of currently available reagent consumption data. The resulting uniform consumption of the reagents in all identically operating treatment stations relieves the user of excessively frequent topping up of the reagents present in the treatment stations that are frequently visited. Several advantages are thus achieved at once.

Regarding the program sequence for a method according to the present invention, the reader is referred to the single FIGURE, in which queries are made, in the event a treatment station is occupied, as to the availability of a backup station. If an unoccupied backup station is available, it is traveled to and occupied. If no backup station is available, serial processing takes place according to a conventional procedure. Further details of the program sequence are evident from the single FIGURE.

The invention has been described in detail with particular reference to certain preferred embodiments thereof, but it will be understood that variations and modifications can be effected within the spirit and scope of the invention.

What is claimed is:

1. In a method for treating cytological or histological specimens in an automatic stainer, the specimens being delivered on object carriers and in object carrier magazines by means of a transport device to various processing stations, inserted therein, and treated in accordance with a definable treatment program, and said transport device being capable, during execution of said treatment program, of moving further objects or object carriers to other processing stations so that a parallel processing or treatment is possible in various processing stations, the improvement comprising the step of:

executing an optimized automatic program sequence according to which identically operating processing stations are defined as backup stations and are correspondingly utilized if a required processing station is occupied, wherein said program sequence takes into account a priority list of identically operating processing stations as backup stations and said priority list is calculated in consideration of defined parameters, wherein the calculation of the priority list is accomplished in consideration of shortest paths.

2. In a method for treating cytological or histological specimens in an automatic stainer, the specimens being delivered on object carriers and in object carrier magazines by means of a transport device to various processing stations, inserted therein, and treated in accordance with a definable treatment program, and said transport device being capable, during execution of said treatment program, of moving further objects or object carriers to other processing stations so that a parallel processing or treatment is possible in various processing stations, the improvement comprising the step of:

executing an optimized automatic program sequence according to which identically operating processing stations are defined as backup stations and are correspondingly utilized if a required processing station is occupied, wherein said program sequence takes into account a priority list of identically operating processing stations as backup stations and said priority list is calculated in consideration of defined parameters, wherein the calculation of the priority list is accomplished in consideration of shortest transport times.

3. In a method for treating cytological or histological specimens in an automatic stainer, the specimens being delivered on object carriers and in object carrier magazines by means of a transport device to various processing stations, inserted therein, and treated in accordance with a definable treatment program, and said transport device being capable, during execution of said treatment program, of moving further objects or object carriers to other processing stations so that a parallel processing or treatment is possible in various processing stations, the improvement comprising the step of:

executing an optimized automatic program sequence according to which identically operating processing stations are defined as backup stations and are correspondingly utilized if a required processing station is occupied, wherein said program sequence takes into account a priority list of identically operating processing stations as backup stations and said priority list is calculated in consideration of defined parameters, wherein the calculation of the priority list is accomplished in consideration of current reagent fill levels in said processing stations.

4. The method as defined in claim 3, wherein said priority list is calculated so as to achieve approximately the same reagent fill levels among said processing stations.

* * * * *